US 011510820B2

(12) United States Patent
Stojanovski

(10) Patent No.: US 11,510,820 B2
(45) Date of Patent: *Nov. 29, 2022

(54) METALLIC BANDAGE

(71) Applicant: Dimitrije Stojanovski, Shelby Township, MI (US)

(72) Inventor: Dimitrije Stojanovski, Shelby Township, MI (US)

(73) Assignee: Dimitrije Stojanovski, Shelby Township, MI (US)

( * ) Notice: Subject to any disclaimer, the term of this patent is extended or adjusted under 35 U.S.C. 154(b) by 448 days.

This patent is subject to a terminal disclaimer.

(21) Appl. No.: 16/460,533

(22) Filed: Jul. 2, 2019

(65) Prior Publication Data

US 2019/0321231 A1 Oct. 24, 2019

Related U.S. Application Data

(63) Continuation-in-part of application No. 16/131,300, filed on Sep. 14, 2018, now Pat. No. 11,304,853, which is a continuation-in-part of application No. 15/842,170, filed on Dec. 14, 2017, now abandoned, which is a continuation-in-part of application No.
(Continued)

(51) Int. Cl.
*A61F 13/00* (2006.01)
*A61F 13/02* (2006.01)

(52) U.S. Cl.
CPC .... *A61F 13/00063* (2013.01); *A61F 13/0206* (2013.01); *A61F 13/0226* (2013.01); *A61F 2013/00234* (2013.01); *A61F 2013/00238* (2013.01)

(58) Field of Classification Search
CPC ........... A61F 13/00063; A61F 13/0206; A61F 13/02; A61F 13/0226; A61F 2013/00234; A61F 2013/00238; A61F 2013/00936; A61F 13/0246; A61F 13/0253; A61F 2013/00089; A61F 13/00; A61K 33/38; A61L 15/42; A61L 15/46; A61L 2300/104; A61L 2300/404; A61L 15/00;
(Continued)

(56) References Cited

U.S. PATENT DOCUMENTS

| 7,214,847 B1 * | 5/2007 | Flick ................. A61F 13/00008 428/103 |
| 11,304,853 B2 * | 4/2022 | Stojanovski ............ A61F 13/02 |

(Continued)

OTHER PUBLICATIONS

Yang et al ("A Novel Silver-Containing Absorbent Wound Dressing based on Spacer Fabric"; J. Mater. Chem. B. 2017, 5, 6786-6793 (Year: 2017).*

*Primary Examiner* — Caitlin A Carreiro
(74) *Attorney, Agent, or Firm* — Quinn IP Law

(57) ABSTRACT

A cloth bandage includes a cloth layer portion including a single weave pattern including a uniform distribution of threads, wherein each thread includes a compound structure including a non-metallic fibrous material and metallic material, and an adhesive layer portion upon a bottom surface of the cloth layer portion configured to adhere the cloth bandage to skin of a wearer. A top surface of the cloth layer portion includes a uniform metallic appearance across the top surface. The metallic material can include silver, copper, or any oligodynamic material.

15 Claims, 11 Drawing Sheets

Related U.S. Application Data

14/989,186, filed on Jan. 6, 2016, now abandoned, which is a continuation-in-part of application No. 14/190,220, filed on Feb. 26, 2014, now abandoned.

(60) Provisional application No. 62/555,264, filed on Sep. 7, 2017, provisional application No. 62/533,887, filed on Jul. 18, 2017.

(58) Field of Classification Search
CPC ...... A61L 15/44; A61L 26/00; A61L 26/0066; A61L 15/58; G06F 3/039
USPC ............ 602/42, 43, 44, 48, 52, 54; 424/443, 424/445–448; 128/888
See application file for complete search history.

(56) References Cited

U.S. PATENT DOCUMENTS

| | | | | |
|---|---|---|---|---|
| 2003/0069369 A1* | 4/2003 | Belenkaya | ................ | D01F 6/92 525/437 |
| 2006/0264796 A1* | 11/2006 | Flick | ..................... | A61F 13/022 602/48 |
| 2011/0137223 A1* | 6/2011 | Daniel | .................... | A61L 15/12 602/76 |
| 2013/0177504 A1* | 7/2013 | Macoviak | ................ | C09D 7/66 424/617 |

* cited by examiner

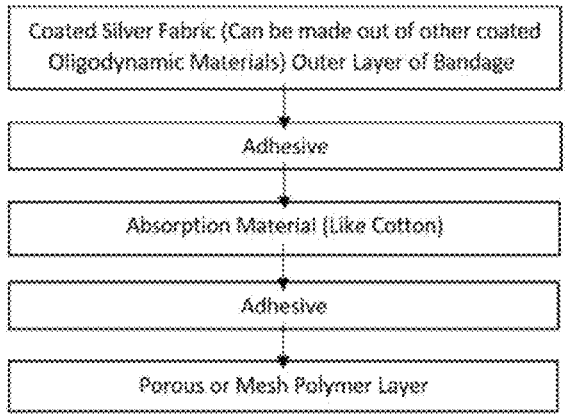
FIG. 13
FIG. 14
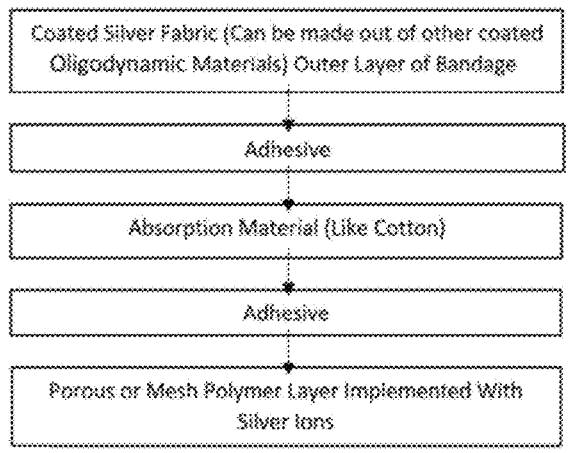
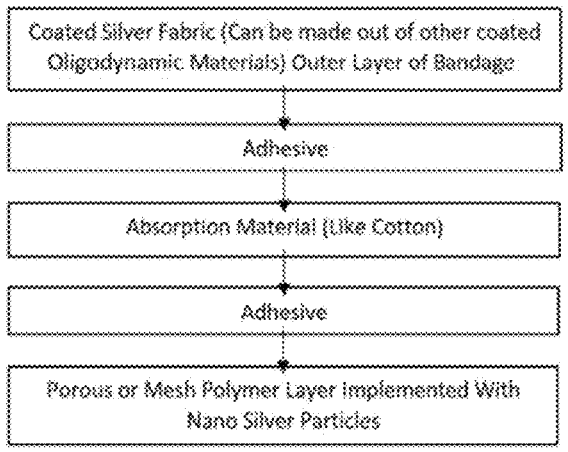
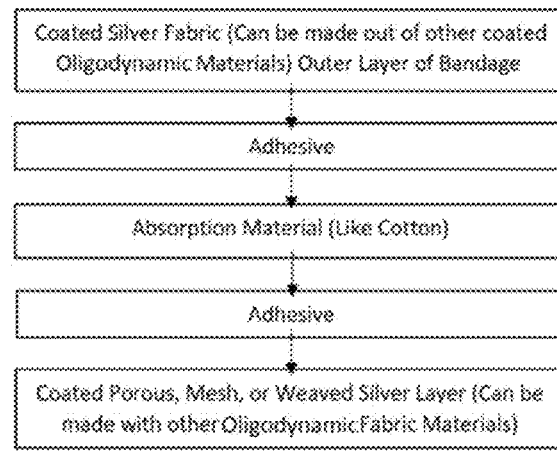
FIG. 15
FIG. 16

METALLIC BANDAGE

CROSS-REFERENCE TO RELATED APPLICATIONS

This disclosure is a continuation-in-part application of U.S. patent application Ser. No. 16/131,300 filed on Sep. 14, 2018 which is a continuation-in-part application of U.S. application Ser. No. 15/842,170 filed on Dec. 14, 2017 which claims priority from both U.S. Provisional Application No. 62/533,887 filed on Jul. 18, 2017 and from U.S. Provisional Application No. 62/555,264 filed on Sep. 7, 2017 and which is a continuation-in-part application of U.S. application Ser. No. 14/989,186 filed on Jan. 6, 2016 which is a continuation-in-part application of U.S. application Ser. No. 14/190,220 filed on Feb. 26, 2014, which are all hereby incorporated by reference.

TECHNICAL FIELD

The present disclosure relates generally to bandages for protection of injured skin. In particular, examples of the present disclosure are related to bandages manufactured with silver treatments to facilitate anti-microbial wound treatment.

BACKGROUND

The statements in this section merely provide background information related to the present disclosure. Accordingly, such statements are not intended to constitute an admission of prior art.

A bandage is a strip of material used to protect, immobilize, compress or support a wound or injured body part. Bandages are available in a wide range of types, from cloth strips to specialized shaped bandages designed for specific body parts or types of injuries. Dressings are materials that are applied directly to wounds to promote healing and prevent further harm to the site of injury.

Typical bandages found in typical home first-aid kits are strips made of plastic, fabric or other suitable materials, with an adhesive side which is placed on the skin and an absorbent pad adhered on the adhesive side which is placed directly over the injured skin. Typical absorbent pads are made out of cotton, polyester or other suitable materials. Other bandages consist of strips of material alone, which do not adhere to the skin but cohere to themselves, for use with separate absorbent pads.

Touchscreen devices employ electronic visual displays that the user can control by touching the screen with a finger or other object such as a stylus. Touchscreens are common in devices such as tablet computers and smartphones. Many touchscreens employ technology that requires an electrically conductive object to touch the screen in order for the user to be able to use the touchscreen device. Human skin is electrically conductive, and can be used to interact with touchscreen devices.

However, certain circumstances arise in which skin must be kept covered. For example, when skin is injured, it is recommended that the skin be kept covered with a bandage. In such circumstances, the wound covering prevents electrically conductive skin from coming into direct contact with touchscreen devices that employ conductive technology, and therefore touchscreen devices can be used only with difficulty when skin must remain covered.

As they are currently manufactured, typical bandages cannot be used with touchscreen devices, as they lack the electrically conductive properties to do so.

Studies have been performed on silver containing dressings. Some studies have shown improvements in wound healing times and healthful results when silver is in contact with a wound site during the healing process.

SUMMARY

A cloth bandage includes a cloth layer portion comprising a single weave pattern comprising a uniform distribution of threads, wherein each thread includes a compound structure including a non-metallic fibrous material and metallic material, and an adhesive layer portion upon a bottom surface of the cloth layer portion configured to adhere the cloth bandage to skin of a wearer. A top surface of the cloth layer portion includes a uniform metallic appearance across the top surface. The metallic material can include silver, copper, or any oligodynamic material.

BRIEF DESCRIPTION OF THE DRAWINGS

One or more embodiments will now be described, by way of example, with reference to the accompanying drawings, in which:

FIG. 1A shows an exemplary woven design of conductive material utilizing straight threads; and FIG. 1B shows an exemplary woven design of conductive material utilizing metallic threads woven at angles;

FIGS. 13-19 illustrate layers of materials and silver treatments that can be utilized to create bandages, in accordance with the present disclosure;

Figure 1A:
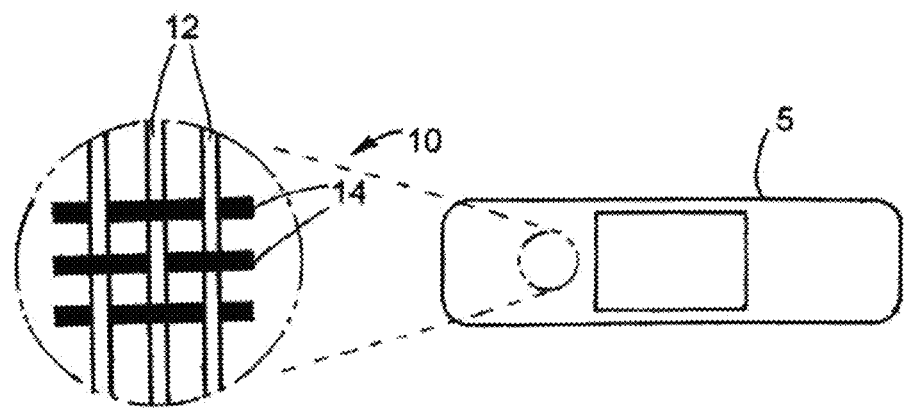
FIGS. 1A and 1B illustrate exemplary designs of conductive cloth for use in bandages that can be used with touchscreen devices, in accordance with the present disclosure.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not illustrated in order to facilitate a less obstructed view of these various embodiments of the present disclosure.

DETAILED DESCRIPTION

In the following description, numerous specific details are set forth in order to provide a thorough understanding of the present disclosure. It will be apparent, however, to one having ordinary skill in the art that the specific detail need not be employed to practice the present disclosure. In other instances, well-known materials or methods have not been described in detail in order to avoid obscuring the present disclosure.

Reference throughout this specification to "one embodiment", "an embodiment", "one example" or "an example" means that a particular feature, structure or characteristic described in connection with the embodiment or example is included in at least one embodiment of the present disclosure. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present disclosure may be embodied as an apparatus or a method.

Metallic thread and other types of conductive materials are not as stretchable as cloth fabric. Conductive materials have been manufactured in a woven pattern that can stretch further than previously known conductive materials. Such patterns take advantage of bends in the threads making up the weaves to compensate for use of a rigid, unstretchable thread. Use of a woven pattern that enables a cloth to stretch is advantageous for embodiments that can benefit both from properties enabled by use of a metallic cloth and properties enabled by using a stretchable material. Retention of such electrically conductive properties is important, for example, for the manufacture of articles that can be used with touch-screen devices.

Metallic materials can be used to provide conductive properties to a bandage. In another embodiment, non-metallic or organic conductive materials can be utilized. An exemplary anti-static conductive polymer adhesive can be used to provide conductivity to a bandage. Similarly, an exemplary conductive silicone rubber or a conductive foam material can be used to provide conductivity. Such products are known in the art and will not be described in detail herein. Such materials need to be selected based upon properties permitting the conductive material to be in close proximity to the skin of a patient according to criteria known in the art related to health care products, such as non-toxicity. Many conductive materials can be utilized according to the disclosed device, and the disclosure is not intended to be limited to the particular examples provided herein.

In addition, metallic and other types of conductive material typically are not breathable, in that they create a barrier which does not allow air to reach the skin or substances to evaporate from the skin. Incorporating metallic and other types of conductive material can be accomplished in a way to allow for a resulting material that retains some breathability, which is important for maintaining healthy and comfortable skin, especially when the skin is wounded and must be kept covered by a bandage.

Typical bandages found in typical home first-aid kits are thin, flexible, stretchable strips of material that come in various shapes and sizes for use with different types of wounds or injuries on different body parts. In general, the bandage has an adhesive face, which contains an adhesive that allows the bandage to adhere to the skin and to itself. An absorbent pad to be placed directly over the site of injury is typically adhered to the adhesive side. This absorbent pad may be made of cotton, polyester, or any other suitable material. The non-adhesive, outside face of the bandage faces away from the skin.

Figure 21:
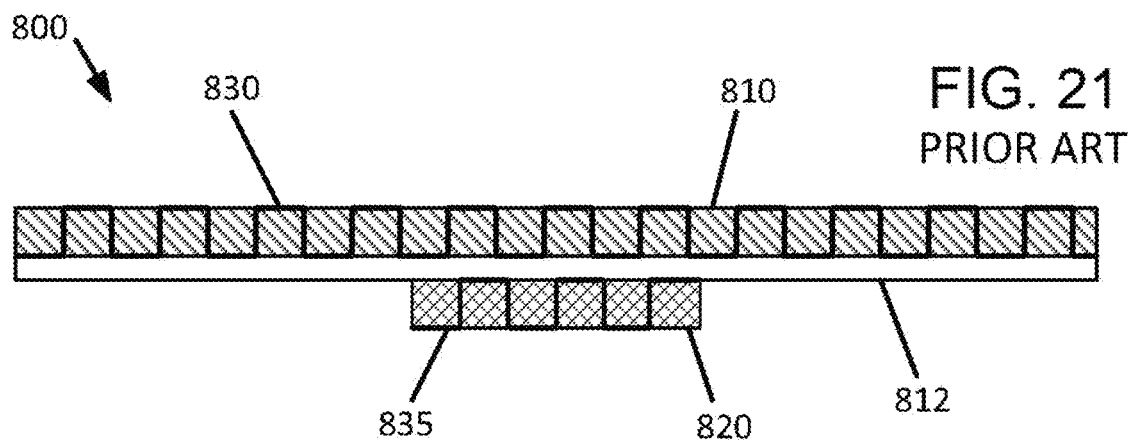
FIGS. 21 and 22 illustrate, in side and top views, respectively, a typical prior art bandage including a primary weave pattern not including any metallic content and with a second weave added to the primary weave including a metallic fiber or thread, in accordance with the present disclosure.
Figure 22:
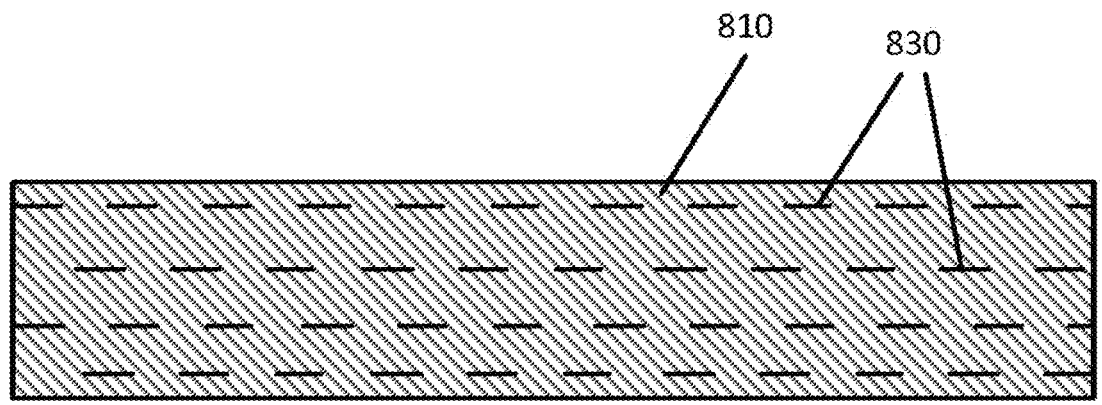

One typical bandage can include a layer including cloth or other material which does not contain any metallic material. Subsequent to this layer of cloth or other material being woven in a primary weave pattern or otherwise initially formed, an exemplary prior art bandage can include a secondary operation to add a strand or a plurality of strands of metallic material to the existing, pre-formed primary weave pattern. FIGS. 21 and 22 illustrate a prior art, exemplary bandage including a cloth layer including a primary weave patterns without any metallic strands included in the primary weave pattern and a secondary weave pattern of metallic strands added to the cloth layer. Bandage 800 is illustrated including cloth layer 810 including only non-metallic cloth formed in a primary weave pattern. The cloth layer, viewed from a top view in FIG. 22, is formed in a generally rectangular shape.

An adhesive layer 812 is provided upon a bottom surface of cloth layer 810, as illustrated in side view in FIG. 21. An absorbent layer 820 is provided attached to a bottom side of bandage 800. One or both of cloth layer 810 and absorbent layer 820 can include a secondary weave pattern of metallic strands 830 and metallic strands 835, respectively.

Figure 23:
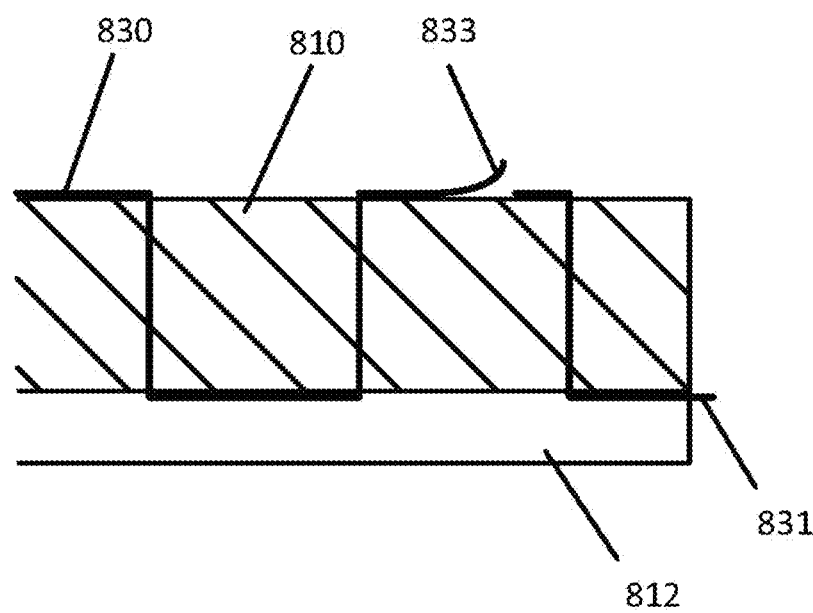
FIG. 23 illustrates the bandage of FIG. 21 including ends of the metallic fiber creating poke obstacles for a user, in accordance with the present disclosure.

While the secondary weave patterns provided by metallic strands 830 and/or 835 would provide effects of having metallic material close to the skin and/or wound of a user, the secondary weave pattern provided by metallic strands 830 and 835 can be problematic, either near sensitive skin of a user or near an open wound site of a user. FIG. 23 illustrates the bandage of FIG. 21 in magnified detail, showing the potential drawbacks of a metallic strand secondary weave pattern. Cloth layer 810 and adhesive layer 812 are illustrated in side view. Metallic strand 830 is illustrated being woven through cloth layer 810. Metallic strand 830 is exposed on an external surface of cloth layer 810, leaving metallic strand 830 open to being snagged or caught upon foreign objects. Further, metallic strand 830, if it is made substantially of metal, is subject to snapping if bent repeatedly or at too sharp of an angle. An end 831 of metallic strand 830 is illustrated poking outwardly from an end of cloth layer 810, and a snapped end 833 of metallic strand 830 is illustrated poking upwardly from cloth layer 810. It will be appreciated that snapped end 833 and similar snapped ends can occur anywhere along a length of metallic strand 830 and can project in any direction from cloth layer 810. As a result, either of end 831 and snapped end 833 can be an irritant, poking and scratching the skin and/or wound of the user.

Touchscreen devices are known in the art and will not be disclosed in detail herein. A touchscreen device is known to sense a location of a user's finger by sensing conduction of electricity from one location on the screen surface, through the finger of the user, and to a second location on the screen surface. In accordance with various embodiments of the present disclosure, an electrically conductive bandage for use with touchscreen devices is provided. A bandage includes conductive material and enables use of a touchscreen device by conducting electricity from one point on the touchscreen device to another point on the touchscreen device.

In some embodiments, the bandage is manufactured with only conductive materials, and any absorbent pad or dressing, whether separate or combined, is manufactured with conventional materials. In one example, such a bandage is manufactured with small holes for ventilation of the skin, to increase breathability for the comfort and health of the user. In other embodiments, any absorbent pad or other dressing combined with the abovementioned bandage also contains conductive material. In further embodiments, both the bandage and any absorbent pad or other dressing combined with the bandage are conductive.

In some embodiments, a layer of conductive material can be deposited or adhered to an outside surface of the bandage. Such a layer, for example, can include a metallic foil. In another example, the layer can include a sprayed on or brushed on layer of conductive material.

In some embodiments, the bandage is made conductive by manufacturing the bandage from a blend of conductive material and conventional materials. In one embodiment, a thread used to make a cloth bandage can include a composite of metallic fibers and conventional fibers, such as cotton or polyester. In another embodiment, a metallic thread can be used in a weave pattern with other non-conductive threads. In other embodiments, the bandage is made conductive by incorporating conductive material into the conventional material of the absorbent pad or other dressing combined with a conventional or conductive bandage. For example, very fine metallic threads can be blended into a cotton absorbent pad. In further embodiments, the bandage is made conductive by first combining conductive particles and adhesive into a mixture and then spraying such a mixture of conductive particles and adhesive directly onto the outside, non-adhesive face of the bandage.

A bandage can conduct electricity along a span of the bandage. Additionally or in the alternative, a bandage can conduct electricity from an outside surface to a contact point with the skin of the wearer in at least two places or points, and the electrical conductivity of the skin of the wearer can be used to complete a conductive circuit between conductive points on the bandage.

Figure 1B:
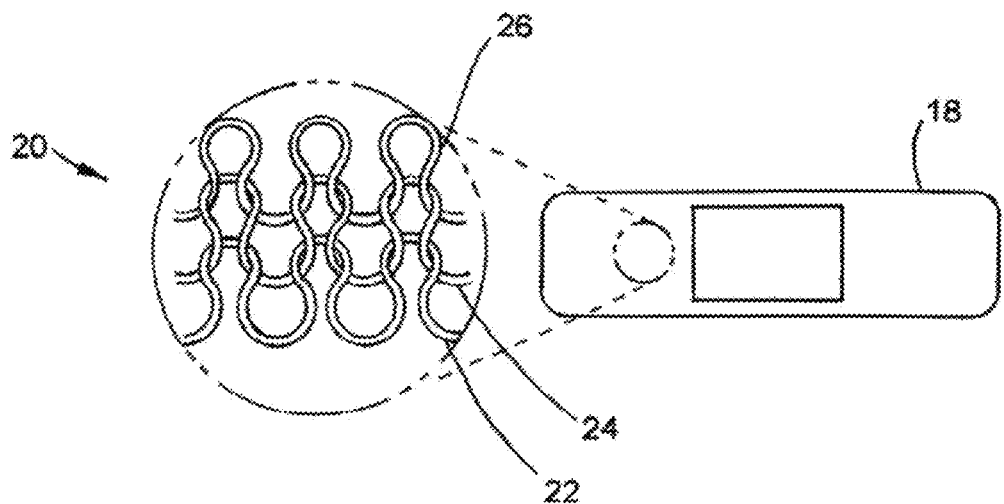

To illustrate, FIGS. 1A and 1B illustrate exemplary designs of conductive cloth for use in bandages that can be used with touchscreen devices.

FIG. 1A shows an exemplary woven design of conductive material utilizing straight threads. Bandage 5 is illustrated including a close up view of fabric 10. Fabric 10 is constructed including a plurality of threads 12 in one direction interlaced with a plurality of threads 14 in another direction, frequently at 90 degree angles to each other. The metallic threads are retained in a straight shape, with threads interwoven at 90 degree angles. In one embodiment, all threads are made conductive material. In other embodiments, some of the threads are made of conductive material and others are made of non-conductive material. Such a woven design is easily and inexpensively constructed. Such a fabric tends to only be elastic if the materials used in the threads are elastic. According to one embodiment, threads 12 can be made of an elastic non-conductive material, such that the fabric is elastic in the direction of those threads, and threads 14 can be made of conductive, inelastic threads providing the touchscreen functionality disclosed herein.

FIG. 1B shows an exemplary woven design of conductive material utilizing metallic threads woven at angles. Bandage 18 is illustrated including a close up view of fabric 20. Fabric 20 is illustrated including a plurality of interwoven threads 22, 24, and 26. In one embodiment, all threads are made conductive material. In other embodiments, some of the threads are made of conductive material and others are made of non-conductive material. Each of the threads bend at after looping with a neighboring thread. When the fabric is pulled in one direction, the threads can flex, giving the fabric stretchability. Fabric 20 permits use of conductive, inelastic threads in a woven fabric, wherein the fabric is elastic due to the construction of the weave.

A number of fabric configurations are known in the art and include a wide variety of thread patterns. A number of different fabric configurations are envisioned for use with the bandages disclosed herein, and the disclosure is not intended to be limited to the particular examples provided herein.

Further embodiments of the present disclosure include bandages made of materials that are manufactured using a combination of conventional non-conductive material that is used in typical non-conductive bandages and the conductive material shown in FIGS. 1A and 1B. For example, such blended material can be made of alternating conductive and non-conductive threads in a variety of patterns and types. Inclusion of non-conductive material would further increase stretchability and breathability of the bandage and can potentially reduce the material costs of the bandage. Stretchability is important for the fit of the bandage over and around the user's site of injury. Breathability is important for the skin surrounding the site of injury to remain healthy. Both stretchability and breathability in bandages can be important for proper healing.

Figure 2A:
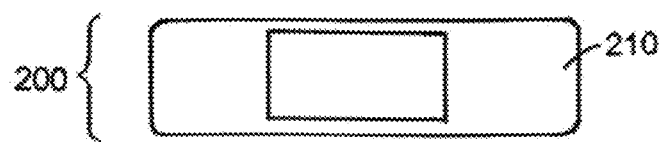
FIGS. 2A and 2B illustrate a top and side view of a bandage manufactured using conductive material, in accordance with the present disclosure.
Figure 2B:
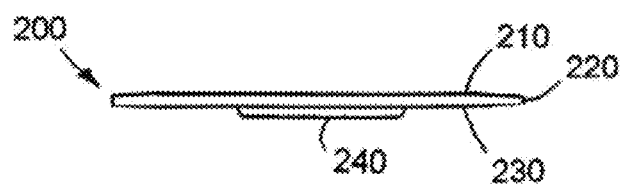

FIGS. 2A and 2B illustrate a top and side view of a bandage manufactured using conductive material, respectively. Bandage 200 has a non-adhesive side 210 that faces away from the skin of the user. FIG. 2B shows bandage 200 including non-adhesive side 210 and adhesive side 230, which adheres to the skin of the user. Absorbent pad 240 is placed over the injured skin of the user to absorb blood and other material, as well as protect the site of injury. Bandage 200 can be made solely of conductive material 230, such as foil. Bandage 200 can be made of a woven material including conductive threads disclosed herein. In some embodiments, the absorbent pad is made entirely of conventional materials, such as cotton. In some embodiments, the absorbent pad 240 may also be manufactured to contain conductive material.

Breathability is especially important in bandages made solely of conductive material, as metallic and other types of conductive material typically are not breathable. Breathability is important for the comfort of the user and the proper wound healing. Therefore, in some embodiments, bandages made solely of conductive materials may be manufactured with small holes or other openings to allow for greater breathability. In another embodiment, a thread density of a woven pattern can be modulated or selected to enhance breathability.

Figure 2C:
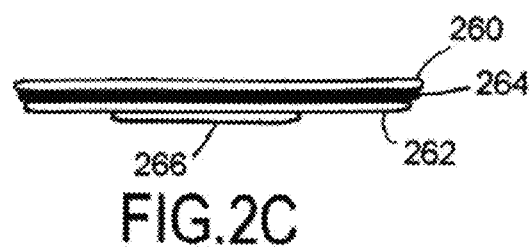
FIG. 2C illustrates a side view of a bandage manufactured using a combination of conductive and non-conductive layers of material, in accordance with the present disclosure.

FIG. 2C illustrates a side view of a bandage manufactured using a combination of conductive and non-conductive layers of material. The conductive and non-conductive materials are not blended or woven together in this embodiment. Instead, in this embodiment, the conductive material 260 is adhered using adhesive material 264 to a typical bandage 262 made of conventional, non-conductive material. The adhesive can be any adhesive known in the art for use within a medical bandage. Typical bandage 262 can be made of cloth, plastic, rubber or other suitable, conventional, non-conductive material that will adhere to the adhesive on the inside face of the conductive material.

Figure 2D:
FIG. 2D shows a side view of bandage manufactured using a combination of conductive and non-conductive materials, wherein non-conductive material is exposed to the touchscreen surface, in accordance with the present disclosure.

FIG. 2D shows a side view of bandage manufactured using a combination of conductive and non-conductive materials, wherein non-conductive material is exposed to the touchscreen surface. In this embodiment, the conductive material 284 is layered between two strips of conventional bandage material 280 and 282. In some embodiments, the conductive material may be layered in various different configurations. In further embodiments, the absorbent pad 288 may be manufactured to contain conductive material. A plurality of conductive zones 286 are illustrated in layer 280, permitting conduction of electricity through each of the zones 286 to the conductive material 284. An electrical circuit is created from a touchscreen surface proximate to one of the conductive zones 286, through the conductive zone 286, through conductive material 284, through the other, second conductive zone 286, and back to the touchscreen surface proximate to the second conductive zone 286. Conductive zone 286 can include some conductive threads interwoven with the material in that area. Conductive zone 286 can include holes with some of the conductive material 284 indented or formed to protrude through the holes. Conductive zone 286 can include an metallic or conductive ionic substance sprayed or brushed on the material.

Figure 2E:
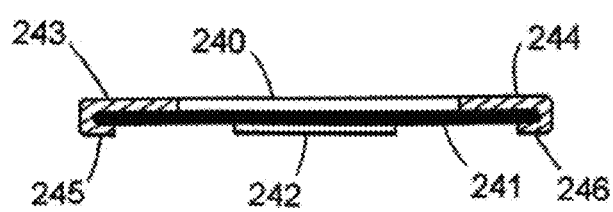
FIG. 2E shows a side view of bandage manufactured using a combination of conductive and non-conductive materials, a conductive layer wraps around at least one side of the bandage, in accordance with the present disclosure.

FIG. 2E shows a side view of bandage manufactured using a combination of conductive and non-conductive materials, a conductive layer wraps around at least one side of the bandage. A bandage is illustrated including a first layer 240 and a second layer 241. An absorbent pad 242 is provided. Layers 240 and 241 can include conductive or non-conductive materials. Two portions of layer 240 include side portions 243 and 244 with conductive materials therein. Each of side portions 243 and 244 include wrap around sections 245 and 246, respectively. Conductivity can be provided or augmented by directly connecting portions 243 and 244 exposed to a phone screen surface to the skin of the patient at the respective wrap around sections. The wrap around sections can be used on one or more surfaces of the bandage to create or augment conductivity across the bandage. The wrap around sections can be threaded metallic fibers, spray or brush on materials, conductive polymers, or any other conductive material as disclosed herein.

Figure 2F:
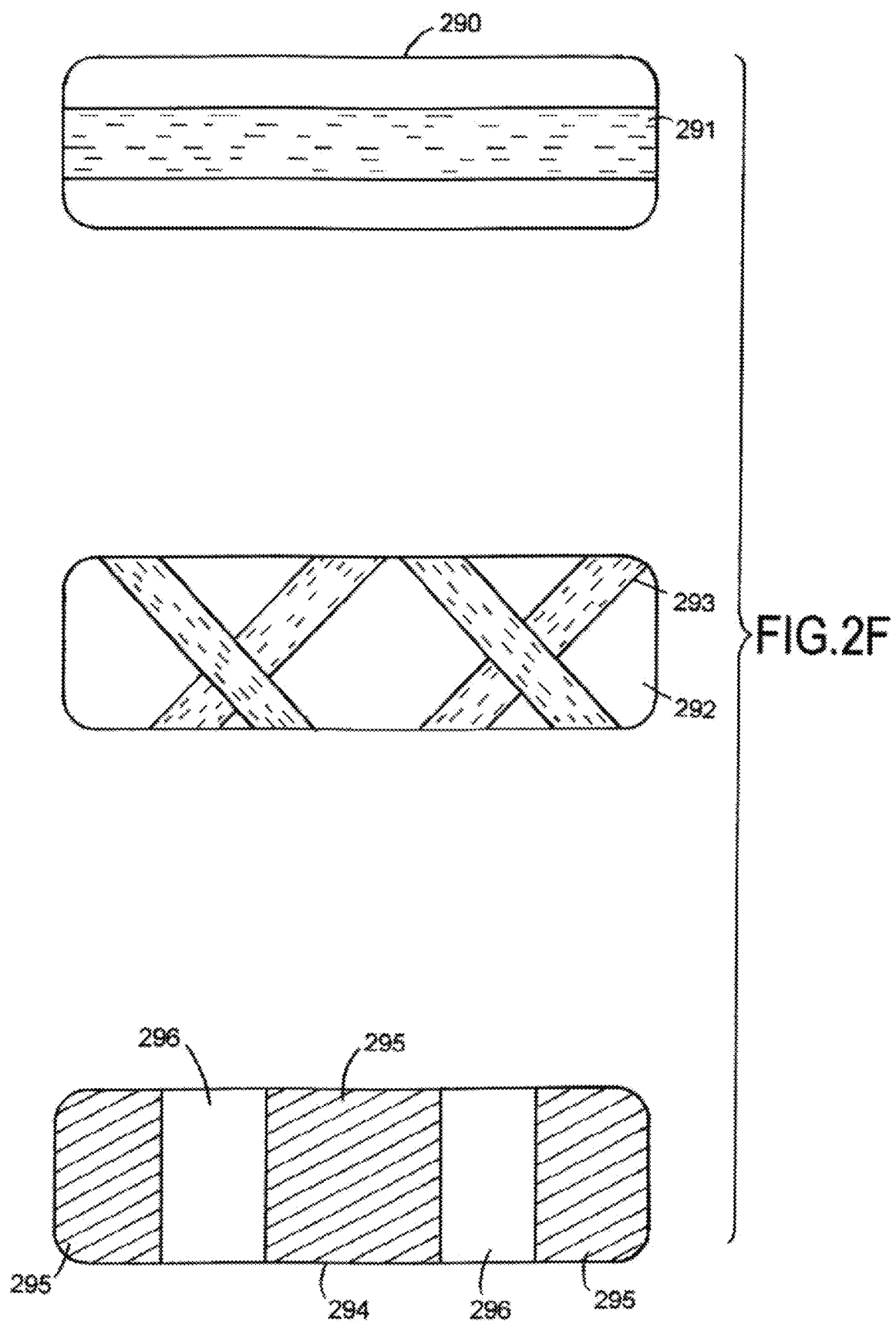
FIG. 2F illustrates a plurality of conductive material patterns that can be provided upon a bandage, in accordance with the present disclosure.

FIG. 2F illustrates a plurality of conductive material patterns that can be provided upon a bandage. Bandage 290 includes a stripe 291 of conductive material running longitudinally along the bandage. Bandage 292 includes a cross-hatch pattern 293 of conductive material. Bandage 294 includes alternating bands of conductive material 295 and non-conductive material 296. The embodiments of FIG. 2F are provided as examples of patterns of conductive material that can be applied or integrated within a bandage. A number of patterns of conductive material are envisioned, and the disclosure is not intended to limited to the examples provided herein.

The exemplary configurations disclosed herein can be used with many types of bandages, for example, a wrap bandage typically used to hold absorbent pads or other material in place. This type of bandage does not adhere to the skin, but rather coheres to itself as it is wound around the injured body part and any absorbent material that has been placed on the skin.

Figure 3:
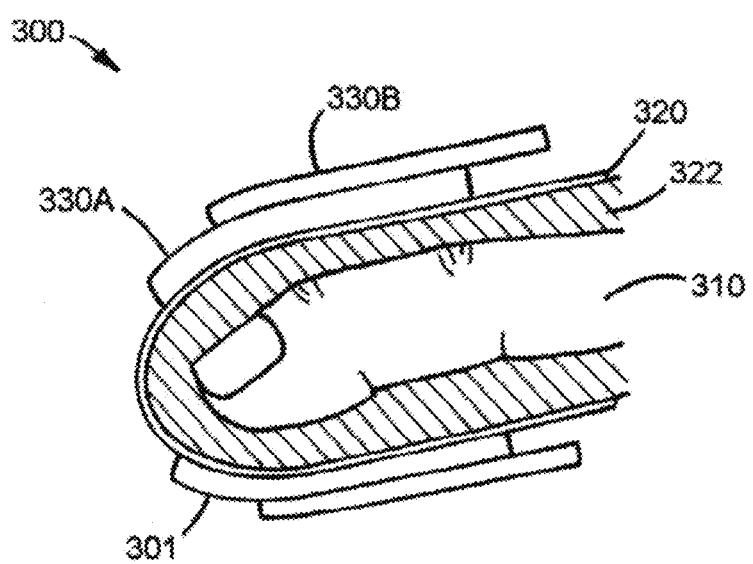
FIG. 3 illustrates a finger wrapped with a bandage configured to wrap around a part of a patient and cohere to itself, the bandage including conductive properties, in accordance with the present disclosure.

FIG. 3 illustrates a finger wrapped with a bandage configured to wrap around a part of a patient and cohere to itself, the bandage including conductive properties as disclosed herein. Configuration 300 includes wrap bandage 301 including conductive threads, a conductive layer, or other means of conductivity as disclosed herein. In the exemplary embodiment of FIG. 3, a finger 310 is encased within a splint device 320 known in the art including padding 322. A first wrap 330A and a second wrap 330B of bandage 301 are shown in cross-section. A similar wrap bandage can be used without the splint device. The wrap bandage 301 includes conductive properties such that finger 310 can be utilized to activate a touch screen device, as disclosed herein.

Figure 4:
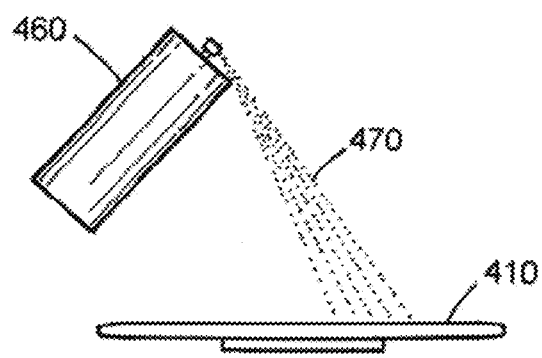
FIG. 4 shows an exemplary bandage with conductive properties, manufactured by spraying conductive material directly onto an outside face of bandage, in accordance with the present disclosure.

FIG. 4 shows an exemplary bandage with conductive properties, manufactured by spraying conductive material directly onto the outside face of bandage. Conductive particles can be mixed with an adhesive spray-able liquid. The adhesive material will allow the conductive particles to be permanently joined to the outside, non-adhesive face 410 of a conventional bandage. As conventional bandages are available in a variety of materials, including fabric, plastic and rubber, among others, various adhesive substances and resulting mixtures may be necessary. The resulting mixture 470 is then sprayed from exemplary spray can 460 directly on the outside, non-adhesive face 410 of a conventional bandage, which faces away from the skin of the user.

Figure 5:
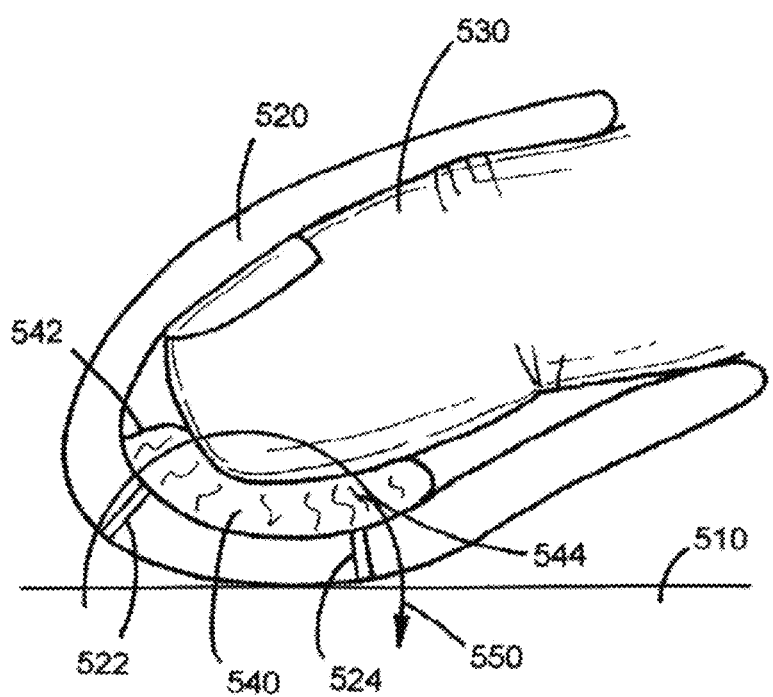
FIG. 5 illustrates an exemplary bandage, wherein conductive material in the bandage permits an electrical circuit to be created through the finger of the wearer, in accordance with the present disclosure.
Figure 6A:
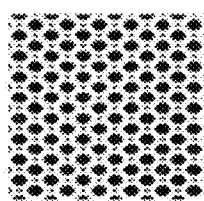
FIGS. 6A-6D illustrate various mesh or porous material patterns that can utilize silver coated fabric located on outer portion of the bandage or fabric coated with other oligodynamic materials, in accordance with the present disclosure.
Figure 6B:
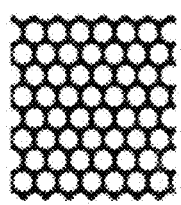
Figure 6C:
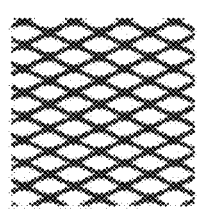
Figure 6D:
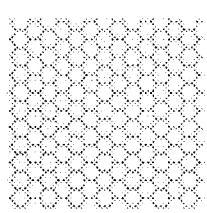

FIG. 5 illustrates an exemplary bandage, wherein conductive material in the bandage permits an electrical circuit to be created through the finger of the wearer. Bandage 520 is illustrated wrapped around and adhered to finger 530. Bandage 520 can be made of generally non-conductive material. Isolated conductive paths 522 and 524 are illustrated providing a path for electrical conduction through bandage 520. In the embodiment of FIG. 5, an adhesive pad 540 is illustrated including conductive material at locations 542 proximate to conductive path 522 and 544 proximate to conductive path 524. Exemplary electrical circuit 550 is illustrated starting in touchscreen surface 510, going through conductive path 522, location 542, finger 530, location 544, conductive path 524, and back into touchscreen surface 510. In one embodiment, the adhesive used to attach the bandage to the skin of the patient can additionally include conductive properties, permitting electrical conduction therethrough. The embodiment of FIG. 5 can be beneficial in that only a small percentage of the material in bandage 520 and pad 540 need be conductive for the embodiment to work as disclosed with a touchscreen device.

Conductive threads, conductive fibers, or conductive can be made of any of a number of conductive materials. Copper, aluminum, or ferrous materials are non-limiting exemplary materials that conduct electricity well and are malleable enough to be used in a flexible bandage.

Conductive threads can be highly conductive, and touchscreen devices only need a small amount of conductivity to sense conduction from one location on the screen to another, so patterns disclosed herein using a blend of conductive and non-conductive threads can include a high percentage of non-conductive threads with only a small percentage of conductive threads. Metallic threads can be expensive relative to a price of normal cloth threads, so such a configuration can incur substantially smaller cost to manufacture as compared to a cloth including most or only metallic threads. In one example, non-conductive threads can make up a majority of the threads in a cloth layer in a conductive bandage as disclosed herein. In another example, non-conductive threads can make up seventy five percent of the threads in a cloth layer in a conductive bandage as disclosed herein. In another example, non-conductive threads can make up ninety percent of the threads in a cloth layer in a conductive bandage as disclosed herein.

In any of the embodiments disclosed herein, silver can be used as all or a portion of the conductive materials used in the bandages. Silver used in dressings has been shown in some studies to aid in the healing process. Silver in the bandages can be used in the cloth layer, the absorbent layer, or both. Silver can be used on an adhesive side of the bandage close to the wound, and another, cheaper conductive material, such as a copper, can be used on the non-adhesive side of the bandage. In such a two material bandage, the threads can be spaced or cross-hatch threaded at 90 degree angles to facilitate electrically conductive contact between the conductive materials, facilitating the touchscreen uses disclosed herein.

Thin strands of silver and/or other conductive materials can be used to make an entire thread for use in a bandage, with a plurality of small strands twisted or braided around each other to make the thread used to weave the cloth of the bandage. A single, larger diameter strand of silver can be used as a thread. A thin strand or a plurality of thin strands can be twisted or braided with other materials to form a composite thread. For example, one silver strand could be braided with a plurality of copper strands. In another example two silver strands could be twisted with cotton fibers to make a thread. A number of different thread configurations are envisioned, and the disclosure is not intended to be limited to the particular embodiments described herein.

Silver is a precious metal. Adding silver to an existing product raises the cost. Further, as a heavily traded commodity, fluctuations in price of silver can make stable manufacturing of a product including silver difficult. Further, excessive exposure to silver, in particular, exposure directly to a user's bloodstream through an exemplary wound, over time can cause adverse reactions. It can be advantageous to provide silver on a product in a concentration sufficient to provide a benefit without using excessive amounts of silver.

Silver in low concentrations can provide silver ions with a therapeutic benefit. A low concentration, for example, as is present in a gauze pad treated with ionic silver, has sufficient silver concentration to provide antimicrobial benefits for a user's skin proximate to the gauze pad. An example of such a gauze pad with ionic silver contained upon the pad includes a ConvaTec® AQUACEL® Ag Surgical Dressing which is described in product paperwork to include "less than 2% ionic silver" and alternatively "De minimus concentration is 1%."

Concentrations herein given in percentages are percentages by weight.

Silver particles or silver ions that separate from a bandage and propagate outward from the bandage upon the skin of the user continue to exhibit antimicrobial properties. Testing was performed using a standard bandage and a bandage using a cloth portion with 30% silver treated fibers. Silver concentration in the cloth portion with the silver treated fibers was between 5-15% of the overall content of the cloth portion. Both samples were placed in Petri dishes in the presence of test bacteria. The standard sample showed bacteria growth all over the sample. The sample with the silver treatment showed not only no bacteria growth on the bandage, but the sample also showed no bacteria growth in a area of approximately two centimeters around the sample. Silver ions from the cloth with the treated threads propagated outward from the sample into the Petri dish and prevented bacteria growth around the sample. Silver in higher concentrations as found on the cloth portion with the silver treated threads can be useful as a reservoir, providing a quantity of silver that can propagate outwardly from the bandage over time to provide antimicrobial properties to the skin around the bandage.

Bandages can be constructed in multiple layers with different percentages of silver concentration in the various layers. Medical benefits can derive from different silver concentrations upon a single bandage. In one exemplary embodiment, a first outer bandage layer can include a cloth or woven layer primarily configured to include adhesive on a lower side of the bandage to secure the bandage to the skin of the user. A second inner bandage layer includes an absorbent pad located on the lower side of the bandage to sit proximate to a wound on the skin of the user and absorb fluids near the wound. According to an embodiment of the disclosure, the cloth layer can include a first silver treatment with a relatively higher silver concentration. The absorbent pad can include a second silver treatment with a relatively lower silver concentration. The absorbent pad provides silver ions directly to the wound site on the skin of the user, while the cloth layer provides a reservoir of silver that can propagate outwardly from the bandage over time.

Figure 20:
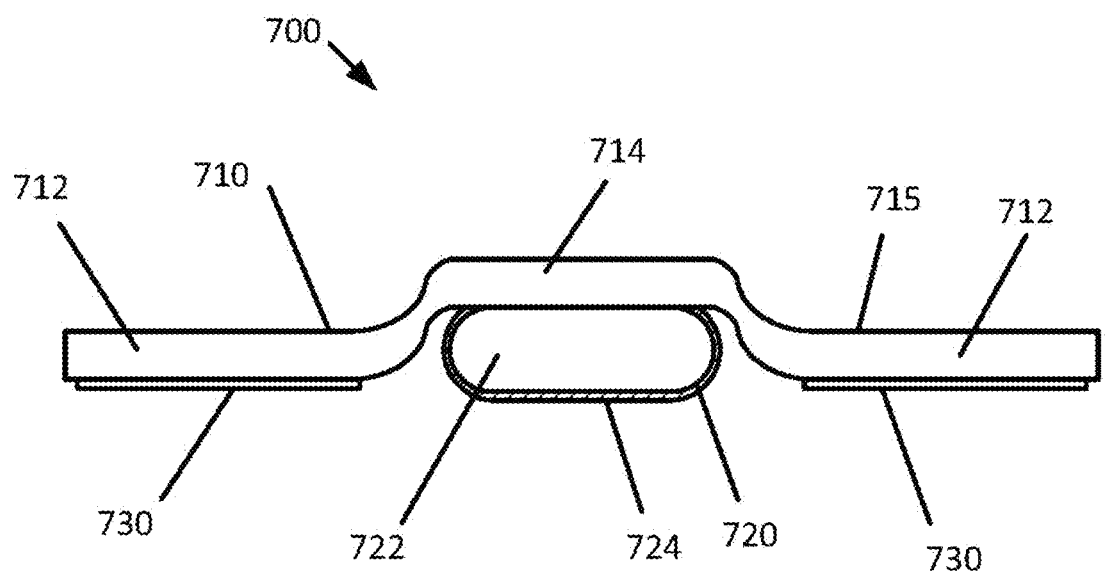
FIG. 20 illustrates in cross section an exemplary bandage with multiple layers with different concentrations of silver treatment upon different portions of the bandage, in accordance with the present disclosure.

FIG. 20 illustrates in cross section an exemplary bandage with multiple layers with different concentrations of silver treatment upon different portions of the bandage. Bandage 700 is illustrated including a cloth portion 710 and an absorbent pad portion 720. Cloth portion 710 includes two side tab portions 712 and one central portion 714. Central portion 714 can be indented or recessed to permit the addition of adhesive pad portion 720 thereto, while permitting a bottom of each side tab portion 712 and a bottom of the absorbent pad portion 720 being nearly co-planar and easy to install to skin of a patient. Absorbent pad portion 720 can include an absorbent material 722 and a thin net layer 724 retaining absorbent material 722 in place. Adhesive layers 730 are illustrated provided upon a bottom of each side tab portions 712.

Various portions of bandage 700 can include silver of different percentages or concentrations. For example, either or both of absorbent material 722 and net layer 724 can include a silver treatment resulting in exemplary 1%-2% silver concentration. Additionally, cloth portion 710 can include threads with a silver treatment, a silver coating upon top surface 715 of cloth portion 710, or any other silver treatment described herein, with a resulting silver concentration of between 5-15%.

Different doctors and different medical circumstances may call for different silver concentrations in bandages—one size fits all is not necessary, and a plurality of silver concentration schemes are envisioned. A variety of silver concentration schemes can be used to define a first silver concentration in a cloth portion of a bandage and a second silver concentration in a pad portion of the bandage. Schemes can include the first silver concentration in the cloth layer being between 1% and 5% by weight, the first silver concentration in the cloth layer being between 5% and 15% by weight, and the first silver concentration in the cloth layer being between 15% and 25% by weight. Schemes can include the second silver concentration in the pad having a thickness of 100 nanometers (nm) or less, the second silver concentration in the pad having a thickness of between 100 nm and 500 nm, the second silver concentration in the pad having a thickness of between 500 nm and 1 micron, the second silver concentration in the pad having a thickness of between 1 micron and 5 microns, and the second silver concentration in the pad having a thickness of greater than 5 microns.

The silver coating on the cloth layer of the bandage threads that make the bandage cloth layer can be coated with common textile coating techniques such as electroless plating, sputtering, dip coating, and nano-coating.

A wide variety of layers and silver treatment methods can be utilized to make bandage 700. FIGS. 13-19 illustrate layers of materials and silver treatments that can be utilized to create bandages in accordance with the present disclosure.

With regard to treating the gauze pad, a number of processes are known for providing very small concentrations of silver or other metals upon a surface such as a bandage surface. For example, electroless plating, sputtering, dip coating, metalizing process and nano-particle techniques known in the art can be utilized. In another embodiment, small amounts of silver can be sprayed or infused into the composition used to make the materials in the bandage surface, such that the bandage is formed with a small concentration of silver particles within the bandage material. In another embodiment, small amounts of silver can be sprayed or infused into the adhesive prior to application to the bandage. The silver can exist as small flecks of silver, a thin layer of silver, or as individual silver ions.

With regard to the cloth layer of the bandage, Silver coated fabric located on outer portion of the bandage (or coated with other oligodynamic materials) can be spun, weaved, braided, and stitched into various patterns to increase flexibility, breathability, and stretch ability of the bandage. FIGS. 6A-6D illustrate various mesh or porous material patterns that can utilize silver coated fabric located on outer portion of the bandage or fabric coated with other oligodynamic materials.

An outer bandage layer can be made from 100% coated threads, a majority of coated threads, or a minority of coated threads. For example, if the threads where made from 50%, 35%, or 20% coated threads. That these threads will be evenly distributed throughout the bandage.

Figure 7:
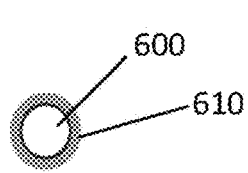
FIG. 7 illustrates in magnified view of a silver coated thread or a thread coated with other oligodynamic materials, in accordance with the present disclosure.
Figure 8:
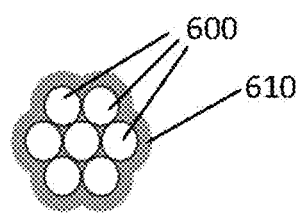
FIG. 8 illustrates a bundle of strands or fibers infused collectively with silver material, in accordance with the present disclosure.
Figure 9:
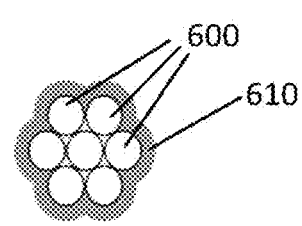
FIG. 9 illustrates a bundle of strands or fibers coated on a periphery with silver material, in accordance with the present disclosure.
Figures 10, 11, 12:
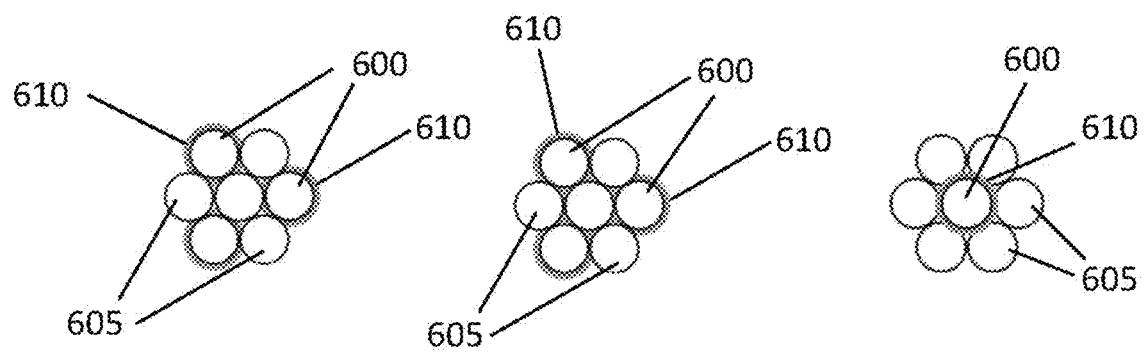
FIG. 10 illustrates a bundle of strands or fibers with some of the strands around a periphery of the bundle are coated with silver material, in accordance with the present disclosure.
FIG. 11 illustrates a bundle of strands or fibers with some of the strands around a periphery of the bundle and in a center of the bundle are coated with silver material, in accordance with the present disclosure.
FIG. 12 illustrates a bundle of strands or fibers with strands not coated with silver material surrounding a core of a fiber or multiple fibers coated with silver material, in accordance with the present disclosure.
Figure 17:
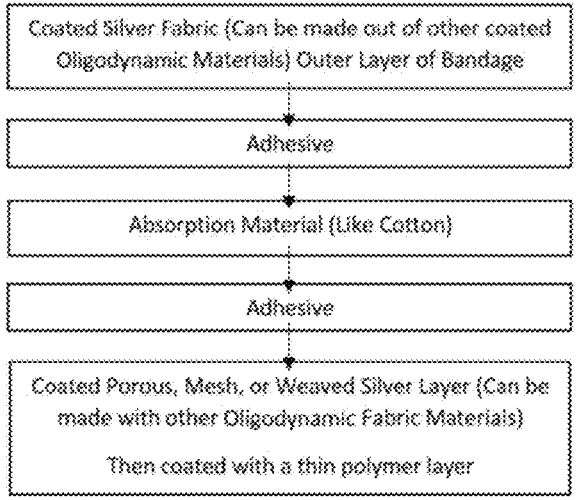
Figure 18:
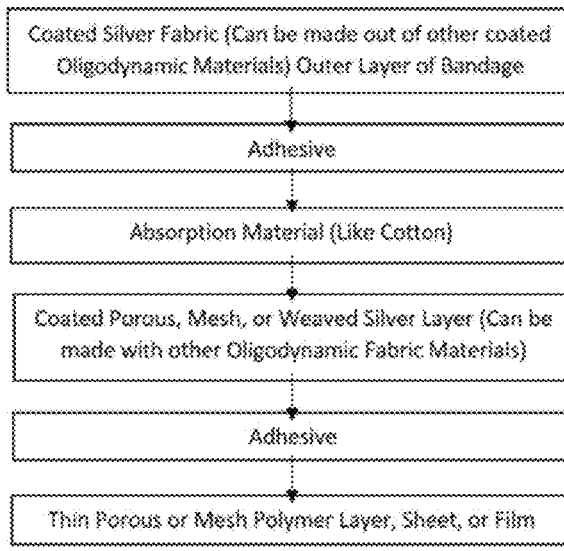
Figure 19:
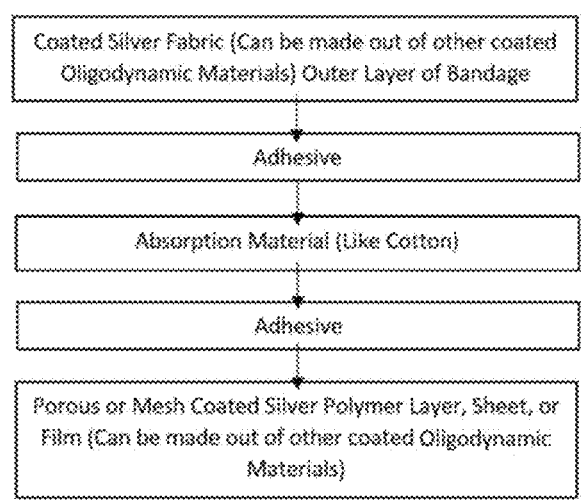

FIG. 7 illustrates in magnified view of a silver coated thread or a thread coated with other oligodynamic materials. Each strand in a fabric can be individually coated. In an alternative embodiment, an outer periphery of several threads can be coated. A single strand 600 is coated with silver material 610. It will be appreciated that silver material 610 is illustrated with significant thickness for the purposes of illustration. In reality, silver material 610 can be provided in different quantities including quantities small enough to not be visible to the naked eye. FIG. 8 illustrates a bundle of strands or fibers infused collectively with silver material. Strands 600 are bundled together, and silver material 610 surrounds the bundled strands and fills interstitial space between strands 600. FIG. 9 illustrates a bundle of strands or fibers coated on a periphery with silver material. Strands 600 are bundled together, and silver material 610 surrounds the bundled strands while no significant silver material 610 fills the space between the strands. FIG. 10 illustrates a bundle of strands or fibers with some of the strands around a periphery of the bundle are coated with silver material. Strands 600 coated with silver material 610 are mixed with strands 605 which are not coated with silver material 610. FIG. 11 illustrates a bundle of strands or fibers with some of the strands around a periphery of the bundle and in a center of the bundle are coated with silver material. Strands 600 coated with silver material 610 are mixed with strands 605 which are not coated with silver material 610. FIG. 12 illustrates a bundle of strands or fibers with strands not coated with silver material surrounding a core of a fiber or multiple fibers coated with silver material. One or more strands 600 coated with silver material 610 can be surrounded with strands not coated with silver material. Various coated thread combinations can be made. Embodiments of bundles of strands illustrated in FIG. 7 through FIG. 12 can be spun, weaved, stitched, or braided together to create bandage fabrics in accordance with the present disclosure.

The threads used in bandage fabrics in accordance with the present disclosure can be constructed with a number of standard fabric or thread materials such as cotton, nylon, and polyester. Additionally or alternatively, antibacterial fiber plants fabric or thread materials such as bamboo and hemp can be used. In place of the cloth layer, a non fabric material like polymers, rubber, latex, or non-latex substitutes can be used. Any combination of the aforementioned materials and common equivalents thereof can be used in bandages in accordance with the present disclosure. Because coated threads to create the fabric can be made with non-coated threads, this gives one the ability to use numerous dye colored threads to create various colors and shades of your bandage. Dyed threads mixed with threads coated with silver do not affect the oligodynamic properties of the bandage.

When the coated threads are equally spaced out you can control the amount silver being used on the bandage fabric and at the same time spread the surface area of the oligodynamic antibacterial properties without limiting its effectiveness against germs. These threads can be made in various mesh, porous, and weaved patterns as illustrated in FIGS. 6A, 6B, 6C, and 6D.

Silver content can be distributed evenly over the cloth layer. In another embodiment, the silver can be distributed over a selected portion or portions of the bandage. For example, silver can be distributed only around a perimeter of the bandage. In another example, the silver coated fabric threads of the cloth layer can have a small amount of surface area coverage of about 15% or less evenly spaced out through the upper cloth layer portion of the bandage. In another embodiment, the silver coated fabric threads of the cloth layer has a small amount of surface area coverage of about 15-35% evenly spaced out through the upper cloth layer portion of the bandage. In another embodiment, the silver coated fabric threads of the cloth layer has a fair amount of surface area coverage of about 35-65% evenly spaced out through the upper cloth layer portion of the bandage. In another embodiment, the silver coated fabric threads of the cloth layer has a large amount of surface area coverage of about 65-85% evenly spaced out through the upper cloth layer portion of the bandage. In another embodiment, the silver coated fabric threads of the cloth layer has a full amount of surface area coverage of about 85% or higher evenly spaced out through the upper cloth layer portion of the bandage.

The absorbent pad portion or layer of a bandage can include a second silver treatment. In one embodiment, the second silver treatment on the absorption pad layer includes a treatment of ionic silver (silver ions) on the any surface or internal portion of the pad. In another embodiment, the second silver treatment on the absorption pad layer, has a treatment of colloidal silver on the top surface of that pad, this silver amount is less than the cloth layer portion. The second silver treatment on the absorption pad layer can be coated with common textile coating techniques such as electroless plating, sputtering, dip coating, and nano-coating.

According to one exemplary embodiment of the disclosure, a cloth bandage is provided including a cloth layer portion an adhesive layer portion upon a bottom surface of the cloth layer portion configured to adhere the cloth bandage to skin of a wearer. The cloth layer portion includes a single weave pattern including a uniform distribution of threads, wherein each thread includes a compound structure including a non-metallic fibrous material and metallic material. A top surface of the cloth layer portion includes a uniform metallic appearance across the top surface.

A cloth layer portion includes a single weave pattern including a uniform distribution of threads, wherein each thread includes a compound structure including a non-metallic fibrous material and metallic material can be described in a number of alternative ways. For example, such a cloth layer portion can be described as a cloth surface including a homogeneous surface including threads constructed of both non-metallic material and metallic material. In another example, such a cloth layer portion can be described as including a woven surface including a plurality of threads, wherein each of the threads includes a uniform metallic content, such that the woven surface includes a uniform metallic appearance. In another example, such a cloth layer portion can be described as including a plurality of cloth threads, wherein each of the cloth threads includes a uniform metallic micro-thread content.

Such a bandage including a cloth layer portion including a single weave pattern can further include an absorbent pad including metallic content in accordance with the present disclosure.

As disclosed throughout this disclosure, cloth layers and threads including metallic content can include silver. Such silver can include micro-thread silver or small fibers of silver spun in with cloth material such as cotton that forms the rest of the thread. Such silver can include silver treatments as described herein. Such silver can include silver coatings as described herein.

As disclosed throughout this disclosure, cloth layers and threads including metallic content can include copper. Such copper can include micro-thread copper or small fibers of copper spun in with cloth material such as cotton that forms the rest of the thread. Such copper can include copper treatments as described herein. Such copper can include copper coatings as described herein.

As disclosed throughout this disclosure, cloth layers and threads including metallic content can include oligodynamic materials. Oligodynamic materials can include but are not limited to silver, gold, copper, brass, and platinum. Such oligodynamic materials can include micro-threads or small fibers spun in with cloth material such as cotton that forms the rest of the thread. Such oligodynamic materials can include coatings as disclosed herein.

The disclosure has described certain preferred embodiments and modifications of those embodiments. Further modifications and alterations may occur to others upon reading and understanding the specification. Therefore, it is intended that the disclosure not be limited to the particular embodiment(s) disclosed as the best mode contemplated for carrying out this disclosure, but that the disclosure will include all embodiments falling within the scope of the appended claims.

The invention claimed is:

1. A bandage including at least two portions with different concentrations of silver treatment upon the at least two portions of the bandage, the bandage comprising:
   a cloth layer portion comprising two side tab portions and one central portion provided therebetween;
   a first silver treatment including a first silver concentration between 15-25%, wherein the first treatment is operable to release silver ions to skin around a wound site of a wearer; and
   an adhesive layer provided upon a bottom surface of each of the two side tab portions of the cloth layer portion and configured to adhere the bandage to the skin around the wound site without contacting the wound site;
   an absorbent pad portion provided on a bottom surface of the central portion of the cloth layer portion such that the absorbent pad portion is operable to contact the wound site of the wearer and separate the cloth layer portion from the wound site of the wearer during use of the bandage, the absorbent pad portion comprising a second silver treatment including a second silver concentration of 1%-2%, wherein the second silver concentration is lower than the first silver concentration and the second silver treatment is operable to release silver ions directly to the wound site;
   wherein the first silver treatment has a relatively higher silver concentration than the second silver treatment so that the cloth layer portion provides a reservoir of silver that can propagate outwardly from the bandage over time to release silver ions to the skin around the wound site and provide antimicrobial properties to the skin around the bandage.

2. The device of claim 1, wherein the cloth layer portion comprising the first silver treatment comprises a layer of silver material upon a top surface of the cloth layer portion.

3. The device of claim 2, wherein the layer of silver material comprises one of an electroless plating layer, a sputtering deposit layer, a dip coating layer, and a nano-coating layer.

4. The device of claim 1, wherein the absorbent pad portion comprises:
   a pad constructed with an absorbent material;
   a net layer material encapsulating the pad constructed with the absorbent material; and
   a layer of silver material upon the net layer material.

5. The device of claim 4, wherein the layer of silver material comprises one of an electroless plating layer, a sputtering deposit layer, a dip coating layer, and a nano-coating layer.

6. The device of claim 1, wherein the cloth layer portion comprising the first silver treatment comprises silver treated threads.

7. The device of claim 1, wherein the first silver treatment is deposited about a perimeter of the cloth layer portion.

8. The device of claim 1, wherein the first silver treatment is limited to a perimeter of the cloth layer portion.

9. The device of claim 1, wherein the second silver treatment comprises a layer of silver having a thickness of less than 100 nanometers.

10. The device of claim 1, wherein the second silver treatment comprises a layer of silver having a thickness of between 100 nanometers and 500 nanometers.

11. The device of claim 1, wherein the second silver treatment comprises a layer of silver having a thickness of between 500 nanometers and 1 micron.

12. The device of claim 1, wherein the second silver treatment comprises a layer of silver having a thickness of between 1 micron and 15 microns.

13. The device of claim 1, wherein the second silver treatment comprises a layer of silver having a thickness of between 15 microns and 30 microns.

14. The device of claim 1, wherein the second silver treatment comprises a layer of silver having a thickness of between 30 microns and 45 microns.

15. The device of claim 1, wherein the absorbent pad portion comprises:
   a pad constructed with an absorbent material;
   a net layer material encapsulating the pad constructed with the absorbent material; and
   a silver material provided within the absorbent material.

* * * * *